(12) United States Patent
Green

(10) Patent No.: US 10,709,873 B1
(45) Date of Patent: Jul. 14, 2020

(54) DEVICE FOR HOLDING A CATHETER IN PLACE

(71) Applicant: Jeanie L. Green, Knoxville, TN (US)

(72) Inventor: Jeanie L. Green, Knoxville, TN (US)

( * ) Notice: Subject to any disclaimer, the term of this patent is extended or adjusted under 35 U.S.C. 154(b) by 248 days.

(21) Appl. No.: 15/424,827

(22) Filed: Feb. 4, 2017

(51) Int. Cl.
*A61B 5/03* (2006.01)
*A61M 25/01* (2006.01)
*A61M 25/02* (2006.01)
*A61M 39/10* (2006.01)
*A61M 25/00* (2006.01)
*A61B 5/00* (2006.01)

(52) U.S. Cl.
CPC .......... *A61M 25/02* (2013.01); *A61B 5/6852* (2013.01); *A61M 25/0017* (2013.01); *A61M 2025/0213* (2013.01); *A61M 2025/0253* (2013.01)

(58) Field of Classification Search
CPC ......... A61B 5/00; A61B 5/6852; A61F 5/453; A61M 2025/0206; A61M 2025/0213; A61M 2025/024; A61M 2025/0253; A61M 25/00; A61M 25/0017; A61M 25/02
See application file for complete search history.

(56) References Cited

U.S. PATENT DOCUMENTS

| | | | | |
|---|---|---|---|---|
| 1,032,611 A | * | 7/1912 | Keyes .................... | A61M 25/02 604/178 |
| 1,661,494 A | * | 3/1928 | Nielsen ................. | A61M 25/02 604/174 |
| 2,604,092 A | * | 7/1952 | Brown ...................... | A01J 1/00 119/852 |
| 3,683,911 A | * | 8/1972 | McCormick .......... | A61M 25/02 128/DIG. 26 |
| 4,337,775 A | * | 7/1982 | Cook ..................... | A61M 25/00 604/102.02 |
| 4,419,097 A | * | 12/1983 | Rowland ................. | A61F 5/453 604/174 |
| 4,519,793 A | * | 5/1985 | Galindo ................ | A61M 25/02 128/DIG. 26 |
| 4,640,688 A | * | 2/1987 | Hauser .................... | A61F 5/453 604/180 |
| 4,767,411 A | * | 8/1988 | Edmunds ............... | A61M 25/02 128/DIG. 26 |
| 4,838,867 A | * | 6/1989 | Kalt ....................... | A61M 25/02 128/DIG. 26 |
| 5,263,947 A | * | 11/1993 | Kay ........................ | A61F 5/451 600/574 |
| 5,531,725 A | * | 7/1996 | Steer ....................... | A61F 5/453 128/844 |
| 5,681,290 A | * | 10/1997 | Alexander ............ | A61M 25/02 604/180 |
| 5,752,944 A | * | 5/1998 | Dann ...................... | A61F 5/453 604/349 |
| 5,795,334 A | * | 8/1998 | Cochrane, III ....... | A61M 25/02 128/DIG. 26 |
| 5,980,507 A | * | 11/1999 | Fassuliotis ............ | A61F 5/4401 604/351 |
| 6,007,526 A | * | 12/1999 | Passalaqua ............. | A61F 5/453 128/844 |
| 9,895,256 B1 | * | 2/2018 | Piterski ................. | A61M 25/02 |
| 2001/0005782 A1 | * | 6/2001 | Tanghoj .................. | A61F 5/453 604/327 |

(Continued)

*Primary Examiner* — Adam Marcetich
(74) *Attorney, Agent, or Firm* — Paul R. Martin

(57) ABSTRACT

A device which is used in place of known catheters, such as the Foley catheter, in tests such as a Urodymics test. The device holds the catheter in place.

2 Claims, 2 Drawing Sheets

(56) References Cited

U.S. PATENT DOCUMENTS

| | | | | |
|---|---|---|---|---|
| 2005/0261642 A1* | 11/2005 | Weston | ............... | A61M 1/0088 |
| | | | | 604/313 |
| 2012/0029451 A1* | 2/2012 | Conway | .................. | A61F 5/453 |
| | | | | 604/349 |
| 2013/0226118 A1* | 8/2013 | Enriquez | ................. | A61F 5/453 |
| | | | | 604/347 |
| 2016/0317359 A1* | 11/2016 | Waller | .................. | A61F 15/008 |
| 2017/0216081 A1* | 8/2017 | Accosta | .................. | A61F 5/453 |
| 2017/0246026 A1* | 8/2017 | Laniado | .................. | A61F 5/443 |

\* cited by examiner

DEVICE FOR HOLDING A CATHETER IN PLACE

TECHNICAL FIELD OF THE INVENTION

The present invention relates to the general art of medical devices, and to the particular field of catheters.

BACKGROUND OF THE INVENTION

Need frequently arises to place a medico-surgical catheter within the urogenital tract of a male patient, or the urinary tract of a female patient, for purposes of treating, testing and monitoring the urologic patient.

These catheters, known in the art as urodynamic catheters, have at least a first pressure-sensing lumen provided with an opening to be positioned in the bladder in order to obtain pressure readings as the bladder is filled with liquid through a fill lumen of the catheter and then as the bladder empties when the patient voids. Typically, urodynamic catheters will also have a second pressure-sensing lumen provided with an opening to be positioned in the urethra for pressure readings.

In the past, urodynamics investigations have been carried out using invasive techniques using, for example, catheters introduced into the bladder. Such catheters can be used for both filling the bladder and directly measuring pressure within the bladder, allowing a comprehensive assessment to be made. However, such invasive techniques are associated with severe patient discomfort, a degree of morbidity, and high cost both in financial terms and in time.

It is found that a proportion of men undergoing prostatectomy do not get the anticipated benefit therefrom and many urologists believe all men should have a urodynamics study beforehand to help identify those less likely to benefit from surgery. There is a real need for a simple, easily administered, atraumatic test which will provide information similar to that currently only available from a full urodynamics study, to give objective evidence of obstruction.

An indwelling urethral catheter is commonplace in hospitals, nursing homes, and various other patient environments. A catheter is a drainage tube placed through the urethra into the bladder. It is utilized for bladder drainage, urinary retention, post-surgery and numerous other scenarios. A catheter is maintained in position by an inflatable balloon at its tip within the urinary bladder of the patient.

Patients in whom these catheters are utilized may be elderly, debilitated, confused or combative. Hence, they may try to pull out the catheter with the inflatable balloon within the bladder resulting in the catheter trauma scenario. This causes prostate and urethra injury requiring immediate intervention; thereafter, pain and infection may ensue. Delayed stricture or scarring may result, also requiring operative means. These sequalae increase patient morbidity.

SUMMARY OF THE INVENTION

These, and other, objects are achieved by a device which is used in place of known catheters, such as the Foley catheter, in tests such as a Urodymics test. The device holds the catheter in place. The device has a body which fits over the head of the patient's penis and is shorter than a normal condom in order to more easily put the catheter in place.

The device of the present invention has a body that is shorter than the normal condom and has a body that is pulled down over the shaft of a man's penis and is attached just behind the head of the penis. The device has a pull tab on a cylindrical end which is removed to leave a residue of adhesive on the device which is used to adhesively attach the device to a catheter by threading the catheter through the cylindrical portion and then squeezing the cylindrical device against the catheter after the tab has been removed.

In this manner, the catheter can be placed inside of the body of the device in order to allow the back of the head to be secured. Once in place, the tab is removed which causes the catheter to slide to the end and not fall out.

More specifically, the device of the present invention is latex free. The device has sticky substance underneath on the inside of the tip, so that when it is pulled and squeezed, it will secure the catheter in place. A line catheter is used for a test, such as a Urodynamics test. A penis goes inside of the body of the device and the sticky substance is used to grip the head of the penis. The sticky substance can be dissolved by applying alcohol so that the device can be removed easier after the test is completed.

The device of the present invention helps give a patient more comfort by having him
experience less pain, which in turn, leads to better testing outcomes and results. The device allows testing to be done while a man is at ease. Since men are more relaxed this device, test results are better.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWING FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENT OF THE INVENTION

Figure 1:
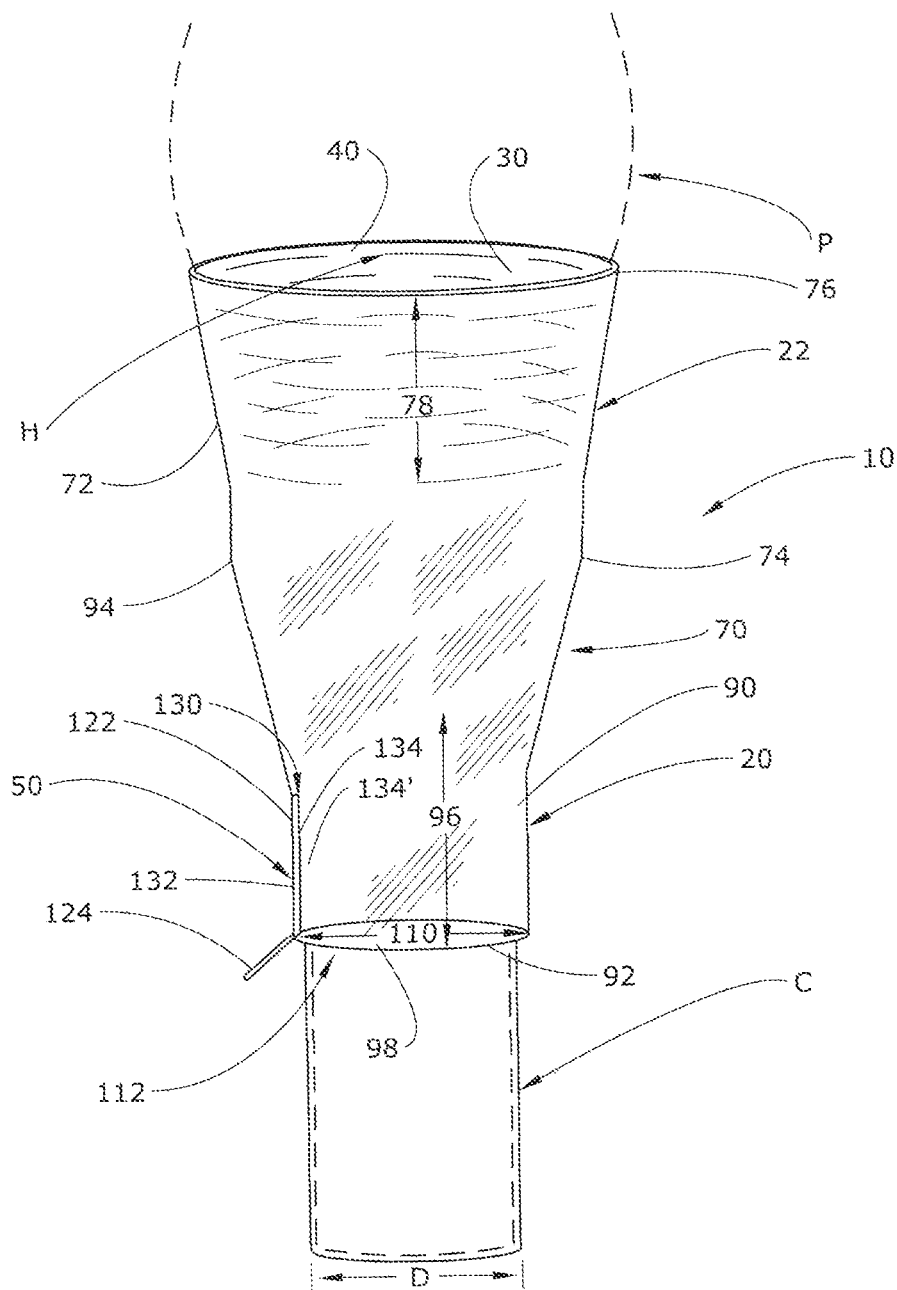
FIG. 1 shows a device for holding a catheter in place embodying the present invention.

Referring to the figures, it can be understood that the present invention is broadly embodied in a device 10 which fits over the head H of a penis P to hold a catheter C in place during testing. Device 10 includes a distal end 20 and a proximal end 22, with a sticky substance 30 located on inside surface 40 of the device. The sticky substance holds the device in place and can be easily removed to remove the device from the subject. A pull tab 50 is located on he inside surface of the device adjacent to distal end 20 and has a water-soluble sticky substance thereon that helps hold the tab on the device. The pull tab hangs out of the device so it can be grasped and pulled to release the device when desired.

More specifically, device 10 comprises a body 70 having a conical portion 72 which is in the form of a frustum of a cone and which has an apex 74, a base 76, a length 78 extending between the apex and the base, and inside surface 40. Device 10 further comprises a hollow cylindrical portion 90 which has an outer end 92, a second end 94 which is unitary with apex 74 of the conical portion, a length 96 which extends between the outer end and the second end of the cylindrical portion, an inside surface 98, and a hollow bore 100 which extends from the outer end to the second end. Inside surface 98 has having an inner diameter 110.

Pull tab 50 has a first portion 122 mounted on inside surface 98 of the cylindrical portion adjacent to outer end 92 of the cylindrical portion. Pull tab 120 further includes a pull portion 124 located outside the hollow bore.

In one form of device 10, adhesive 130 releasably mounts the pull tab to the inside surface of the cylindrical portion. Adhesive 130 includes a first portion 132 which is secured to the pull tab and a second portion 134 which is secured to inside surface 98 of the cylindrical bore. First and second portions of the adhesive have adhesive properties, with the adhesive property of the second portion of the adhesive being selected so that at least a portion of the second portion of adhesive, designated as 134' in FIG. 1, remains in place on the inside surface of the cylindrical portion when the pull tab is separated from the cylindrical portion. The adhesive properties of the portions of adhesive 130 can be selected from known disclosures, such as http://www.adhesivestool-kit.com/Docu-Data/AdhesiveTypesOverview.xtp, or from the patent literature, such as U.S. Pat. No. 7,886,571, or from literature such as Bhushan, "Thin film friction and adhesion studies using atomic force microscopy. February 2000, Journal of Applied Physics, vol. 87, No. 3, or the like, with the cited references in the just-mentioned patent '571, also being incorporated herein by reference.

In another form of the device 10, the tab forms a release structure which is separated from the inside surface 98 leaves some adhesive on that inside surface. Such structures are known in the art .from disclosures such as US Published Patent Application Number 20140302269, the disclosure of which is incorporated herein by reference. As disclosed in the incorporated document, '269.: "Release surfaces are well known, for example in the pressure sensitive adhesive tape industry to provide a release surface so that a tape can be unwound from a roil without the adhesive sticking to the backside of the tape. The release coating can also be coated onto a liner which. serves as a. carrier for a pressure sensitive adhesive transfer tape or a double coated tape, both of which are tacky on 'both sides of the tape. Release surfaces are also useful as a release liner for use with pressure sensitive adhesive films.

Materials. commonly used for release surfaces and coatings. are silicone compositions because they can be formulated to provide 'Varying levels of release from a "premium" release (i.e., the force to unwind the tape is very low) to a "low adhesion backsize" release which typically requires a. greater force to unwind. Polyethylene has also been used as a release material and can be coated onto Kraft papers for a release liner or it can be used as a single layer film, or a multi-layer film with polyethylene co-extruded with or laminated to a base layer .such as high density polyethylene, and the like,"

Catheter C has an outer diameter 13, with inside diameter 110 of the hollow bore of the cylindrical portion being larger than the outer diameter of the catheter so that a gap 112 is defined between the catheter and the inside surface of the cylindrical portion when the catheter is first inserted through the hollow bore and before the device is set.

The portion of the second portion 134 of the adhesive which remains on the inside surface of the bore adhesively secures the cylindrical portion to the outside surface of the catheter when the hollow cylindrical portion of the body is in abutting contact with the catheter.

Figure 2:
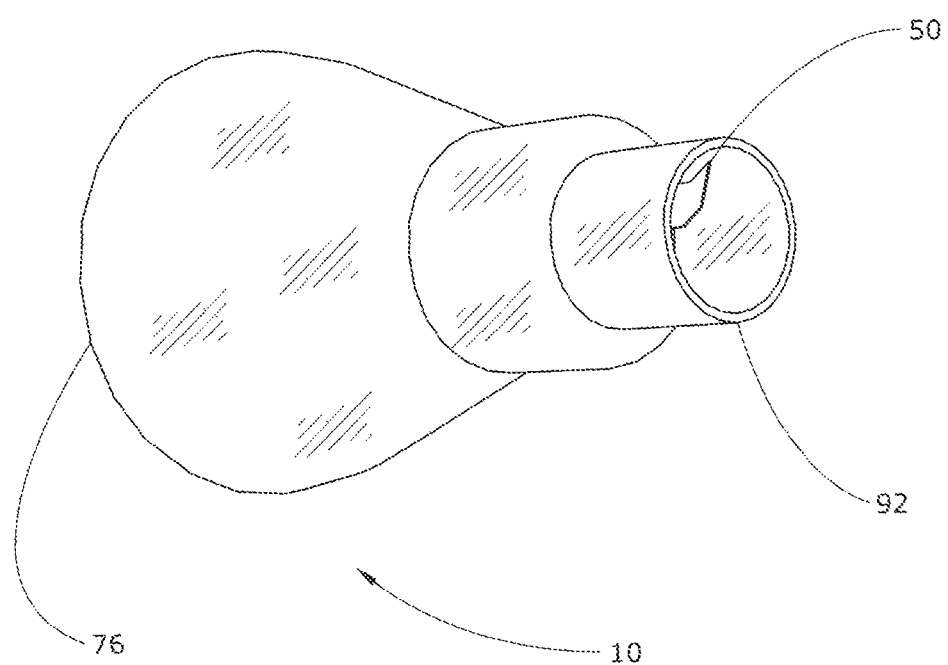
FIG. 2 is another view of the device embodying the present invention.

The tab allows the device 10 to be much shorter than previous devices and thus much easier to apply and remove. The tab is located on the inside of the cylindrical portion adjacent to the distal end and extends from the outer end toward the conical body. The conical body is shaped to fit over the end of a patient's penis and to extend downwardly just far enough to securely hold a catheter in place. The adhesive 30 on the inside surface of the conical portion releasably attaches that portion of the device to the patient's penis and secures the device in place. The adhesive 30 works in conjunction with the adhesive portion 134 attaching the cylindrical portion of the device to the catheter to ensure a firm, yet comfortable, attachment of the catheter to the patient. Because of this dual attachment, the overall size and length of device 10 is much shorter than the length of a condom and thus device 10 is much easier to place and remove than a condom while being comfortable to place, wear and remove than a condom. The average length of a penis head is between 1.5" to 1.6" with an outer length being between 0.5" and 3". After the device is placed, the device should cover the penis head and extend for approximately ½, inch subadjacent to the head. Thus, the length the conical body as measured from apex 72 to base 74 is between 2.0" and 2.1" as opposed to many inches for a usual condom which is intended to cover the entire penis from head to root. In special cases for extremely large of extremely small penises, the just-mentioned lengths can be modified accordingly. As can be understood from FIG. 2, the overall length of the device is much shorter than a normal condom, with the conical portion being just long enough to cover the head of the patient's penis.

Once the device is placed on a patient's penis by fitting the conical portion of the device over the end of the patient's penis and allowing the adhesive to attach that conical portion to the penis just subadjacent to the penis head, the catheter is threaded through the hollow bore of the cylindrical end and into the glans of the patient's penis. The pull portion of the tab is grasped and the tab is pulled off of the inside surface of the cylindrical portion leaving a residue of adhesive on inside surface of the cylindrical portion. The cylindrical portion is then squeezed inwardly toward the catheter to abuttingly engage the adhesive residue on the inside surface of the cylindrical portion with the outside surface of the catheter and adhesively attach the device 10 to the positioned catheter and thus securely mount the catheter to the patient.

All of the adhesive used in conjunction with device 10 is soluble so the device can be easily released from the catheter and from the patient. Since the penis may be wet during use of device 10, the adhesive should not be water soluble.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

What is claimed is:

1. A medical device configured for holding a catheter comprising:
    a body having
        a conical portion having an apex, a base, a length extending between the apex and the base, a first end, a second end, and an inside surface,
        a first adhesive on the inside surface of the conical portion adjacent to the first end of the conical portion, a hollow cylindrical portion having an outer end, a second end which is unitary with the apex of the conical portion, a length which extends between the outer end and the second end of the cylindrical portion, an inside surface, and a hollow bore which extends from the outer end to the second end of the cylindrical portion, the inside surface of the cylindrical portion having an inner diameter, a pull tab having a first portion mounted on the inside surface of the cylindrical portion adjacent to the outer end of the cylindrical portion, the pull tab further having a pull portion located outside the hollow bore;

a second adhesive releasably mounting the pull tab to the inside surface of the cylindrical portion, the second adhesive being spaced apart from the first adhesive on the conical portion so that the inside surface of the conical portion is free of adhesive between the adhesive adjacent to the first end of the conical portion and the cylindrical portion, the second adhesive including first and second portions, the second adhesive first portion being secured to the pull tab and the second adhesive second portion being located on the inside surface of the bore of the hollow cylindrical portion, the second adhesive first portion having adhesive properties selected so that the at least a portion of the second adhesive second portion remains in place on the inside surface of the cylindrical portion when the pull tab is separated from the cylindrical portion;

a catheter having an outside surface having an outer diameter, the inside diameter of the hollow bore of the cylindrical portion being larger than the outer diameter of the catheter so that a gap is defined between the outside surface of the catheter and the inside surface of the cylindrical portion when the catheter is first inserted through the hollow bore;

the second adhesive second portion remaining on the inside surface of the cylindrical portion of the body having adhesive properties to releasably secure the cylindrical portion to the outside surface of the catheter when the catheter is in abutting contact with the inside surface of the cylindrical portion of the body.

2. A medical device for holding a catheter comprising:

a catheter having an outside surface and an outer diameter of the outside surface of the catheter; a device for holding a catheter, the device including a body having a conical portion having an apex, a base, a length extending between the apex and the base, a first end, a second end and an inside surface, a first adhesive on the inside surface of the conical portion adjacent to the first end, and a hollow cylindrical portion having an outer end, a second end which is unitary with the apex of the conical portion, a length which extends between the outer end and the second end of the cylindrical portion, an inside surface, and a hollow bore which extends from the outer end to the second end of the cylindrical portion, the inside surface having an inner diameter;

a pull tab having a first portion mounted on the inside surface of the cylindrical portion adjacent to the outer end of the cylindrical portion, the pull tab further having a pull portion located outside the hollow bore;

a second adhesive releasably mounting the pull tab to the inside surface of the cylindrical portion, the second adhesive being spaced apart from the first adhesive on the conical portion so that the inside surface of the conical portion is free of adhesive between the adhesive adjacent to the first end of the conical portion and the cylindrical portion, the second adhesive including first and second portions, the second adhesive first portion being secured to the pull tab and the second adhesive second portion being located on the inside surface of the hollow cylindrical portion, the second adhesive first portion having adhesive properties selected so that the at least a portion of the second adhesive second portion remains in place on the inside surface of the cylindrical portion when the pull tab is separated from the cylindrical portion;

the inside diameter of the hollow bore of the cylindrical portion being larger than the outer diameter of the catheter so that a gap is defined between the catheter and the inside surface of the cylindrical portion when the catheter is first inserted through the hollow bore;

the second adhesive second portion remaining on the inside surface of the cylindrical portion of the body having adhesive properties to releasably secure the cylindrical portion of the body to the outside surface of the catheter when the catheter is in abutting contact with the inside surface of the cylindrical portion of the body;

wherein the gap is sized to loosely accommodate the pull tab when the cylindrical portion of the body surrounds the catheter whereby the tab can be removed from the inside surface of the cylindrical portion of the body when the catheter is located within the cylindrical portion of the body.

\* \* \* \* \*